United States Patent [19]
Harris et al.

[11] Patent Number: 6,038,978
[45] Date of Patent: Mar. 21, 2000

[54] SHOTSHELL HAVING A PROTECTIVE BARRIER LAYER

[75] Inventors: Melvin Ward Harris, Worden, Ill.; Scott Hayward Mayfield, Creve Coeur, Mo.

[73] Assignee: Olin Corporation, East Alton, Ill.

[21] Appl. No.: 09/022,233

[22] Filed: Feb. 11, 1998

[51] Int. Cl.[7] ............................................ F42B 5/30
[52] U.S. Cl. .................... 102/467; 102/430; 102/464
[58] Field of Search ................................. 102/430, 435, 102/446, 448–467

[56] References Cited

U.S. PATENT DOCUMENTS

| | | | |
|---|---|---|---|
| 272,581 | 2/1883 | Piffard | 102/464 |
| 339,306 | 4/1886 | Libbey | 102/464 |
| 563,157 | 6/1896 | Gardner . | |
| 1,196,200 | 8/1916 | Batcher | 102/462 |
| 3,076,409 | 2/1963 | Williams et al. | 102/43 |
| 3,162,125 | 12/1964 | Lewis et al. | 102/467 |
| 3,170,401 | 2/1965 | Johnson et al. | 102/467 |
| 3,332,352 | 7/1967 | Olson et al. | 102/467 |
| 3,550,532 | 12/1970 | Zimmerman | 102/43 |
| 3,646,887 | 3/1972 | Stine | 102/504 |
| 3,678,858 | 7/1972 | Herter et al. | 102/43 |
| 3,722,412 | 3/1973 | Herter | 102/43 |
| 3,749,021 | 7/1973 | Burgess | 102/467 |
| 3,996,865 | 12/1976 | Dwyer | 102/460 |
| 4,068,589 | 1/1978 | Oversohl | 102/43 |
| 4,593,622 | 6/1986 | Fibranz | 102/530 |
| 4,656,948 | 4/1987 | Tsukiuda et al. | 102/452 |
| 4,942,817 | 7/1990 | Ikeda et al. | 102/331 |
| 4,991,512 | 2/1991 | Van Wyk | 102/466 |

FOREIGN PATENT DOCUMENTS

| | | | |
|---|---|---|---|
| 540698 | 8/1959 | Belgium | 102/467 |
| 780821 | 5/1935 | France | 102/464 |
| 12537 | of 1890 | United Kingdom | 102/450 |

OTHER PUBLICATIONS

Winchester AA SILVER Shotshell Label, BW Italia, S.p.A.

*Primary Examiner*—Harold J. Tudor
*Attorney, Agent, or Firm*—Gregory S. Rosenblatt; Wiggin & Dana

[57] ABSTRACT

A shotshell having a hull with a protective barrier layer of fiber or other alternate material that prevents the hull from being in contact with the chamber. The protective layer may cover any portion of the exterior of the hull. The protective layer protects the plastic hull from the hot chamber of the barrel that would adversely affect the structural integrity or functioning of the shotshell. The protective material may be of precut size and thickness that when applied to the exterior of the hull will increase the diameter to reduce the clearance with the chamber and thereby resist sliding out of the chamber before the breech is closed. The protective layer may also have an adhesive surface disposed between the exterior surface of the hull and the protective layer to prevent the separation of the hull and the protective material.

19 Claims, 7 Drawing Sheets

SHOTSHELL HAVING A PROTECTIVE BARRIER LAYER

BACKGROUND OF THE INVENTION

1. Field of the Invention

This invention relates to a shotshell for expulsion of material from a barrel. More particularly, a portion of a plastic hull has a layer of a material that adheres to an exterior surface of the hull protecting the hull from the chamber of the barrel. This configuration prevents the plastic hull from exposure to heat that would adversely affect the structural integrity of the hull.

2. Description of the Art

Industrial ammunition such as lead, zinc or steel slugs, are used to assist industry in the area of rotary kilns and furnace tapping.

U.S. patent application Ser. No. 08/862,048 by Dippold et al. filed May 22, 1997 discloses a metallic slug for industrial ballistic tool. This application is incorporated by reference in its entirety herein.

Projectiles, such as pellets or a single slug, are loaded into a cavity in the hull during the shotshell manufacturing process and the assembled shotshell is placed into a the chamber by an operator to be discharged from the muzzle end of the barrel.

Conventional plastic shells are not satisfactory when used in elevated temperature conditions, such as those caused by rapid continuous firing or external furnace heat, because the high temperatures may melt or soften the plastic hull. This causes an undesirable plastic residue from the hull that can accumulate in the chamber of a firing apparatus such as a gun or industrial tool. A second drawback of a conventional plastic shotshell is that with the muzzle of a barrel elevated, typically more than 10 degrees, the conventional plastic shell has a tendency to slide backwards out of the chamber before the breech can be closed.

U.S. Pat. No. 3,076,409 (Williams et al.) discloses a spiral wound shotshell. This patent discloses a tubular body fabricated from three distinct layers of materials where all of the layers are laminated together to produce a composite or laminated tube. The outer layer is made of materials such as polyolefin films, cellophane, polyester films and metallized films. The intermediate layer is formed from materials such as metal foils, paper reinforced with fiberglass, paper and polyolefin laminate. The inner layer is formed of materials such as waxed paper, film laminates, paper and foil laminates. The layers are formed by spirally winding band or ribbon-like materials where each layer is wound with a given lead and with a given hand.

U.S. Pat. No. 563,157 (Gardner) discloses a paper-shell cartridge having a paper tube and drawn sheet-metal cap, which is continuously upset around its circumference.

These patents fail to disclose a shotshell having a hull with a layer of material adhering to a portion of the exterior of the hull thereby preventing contact between the hull of the shotshell and the chamber. Specifically, none of the prior art discloses a paper layer wrapped around a plastic shotshell hull.

As can be seen from the present state of the art, there exists a need for an improved shotshell that overcomes the inadequacies of the prior art.

BRIEF SUMMARY OF THE INVENTION

An object of the present invention is to provide an improved shotshell that prevents buildup caused by the melting of a hull in a hot firing chamber.

Accordingly, in one aspect the invention is directed to a shotshell having a projectile, a propellant charge, and a hull. A plastic portion of the hull extends for a substantial portion of the length of the hull and accommodates the projectile in a front portion and the propellant charge in an aft portion. A protective material selected from the group consisting of metallic foils, paper, and fiberglass is adhered to an exterior surface of the plastic portion.

Optionally, in various implementations of the invention, the protective material may adhere to at least approximately 5% of the exterior surface of the hull. An adhesive material may be disposed between the protective material and the exterior of the hull for adhering the protective material to the exterior surface of the hull. The adhesive material may be pressure-sensitive. The protective material may have a thickness effective to only slightly increase the diameter of the shotshell. The protective material may adhere to approximately 50% or more of the exterior surface. The protective material may adhere to between 5% and 50% of the exterior surface area. The protective material may have a thickness of between about 0.002 inches and about 0.004 inches. The protective material may form a tube-like structure that is slid over the exterior surface. The protective material may not cover an exterior surface of the hull from a terminal end of the hull for a distance of about 3% of the length of the hull. The protective material may be non-combustible below a temperature of 400° F. The protective material may be pre-cut to a particular size so as to adhere to over 5% of a surface area of an exterior surface of the hull. The protective material may surround less than the entire circumference of the shotshell. The shotshell may be an industrial shotshell, dimensioned for use in an eight-gauge industrial ballistic tool.

In another aspect, the invention is directed to an industrial shell for use with an industrial ballistic tool. The shell includes a projectile and a hull having a plastic portion extending for a substantial portion of the length of the shell and having a front portion holding the projectile and an aft portion enclosing a propellant charge. A protective member substantially surrounds and is adhered to an exterior surface of the plastic portion and comprises a material selected from the group consisting of metallic foils, paper, and fiberglass.

Optionally, in various implementations of the invention, the shell may be dimensioned for use with an eight-gauge industrial ballistic tool. The projectile may be a single industrial slug. The presence of the material may reduce a tendency of the shell to slide out of the chamber of the tool when a muzzle of the tool is elevated. The material may be effective to insulate the hull from exposure to heat from the chamber of the tool.

In another aspect, the invention is directed to a method for preparing a shotshell for discharging from a firing chamber. A hollow hull is formed having proximal and terminal ends and exterior and interior surfaces. A metallic cap is formed at the proximal end of the hull for receiving a primer. A protective material layer is formed adhering to a portion of the exterior surface of the hull. The protective material layer is selected from the group consisting of paper, metallic foil, and fiberglass. The protective material provides a barrier between a plastic portion of the hull and the firing chamber and has substantially greater resistance to melting and softening than does the plastic portion when contacted with the chamber having a temperature elevated by repeated firing. The protective layer has a thickness effective to only slightly increase a diameter of the shotshell.

DETAILED DESCRIPTION

Shotshells, having plastic hulls, used in rotary kilns and furnace tapping, experience some melting or softening while in the chamber of the firing apparatus due to heat generated during repeated firing of the industrial tool. Upon firing, the projectiles of the shotshell are discharged from the muzzle end of the barrel and the shotshell is expelled from the chamber end of the barrel. Some of the plastic of the hull will soften or melt leaving a residue in the chamber. This residue can build up over time, making it increasingly difficult to insert and remove subsequent shotshells. This residue can be difficult and time consuming to remove.

The present invention solves this problem by disposing a layer of protective material in a sleeve-like configuration around the hull. This protective material adheres to the exterior surface of the hull providing a barrier between the hull and the chamber.

Figure 1A:
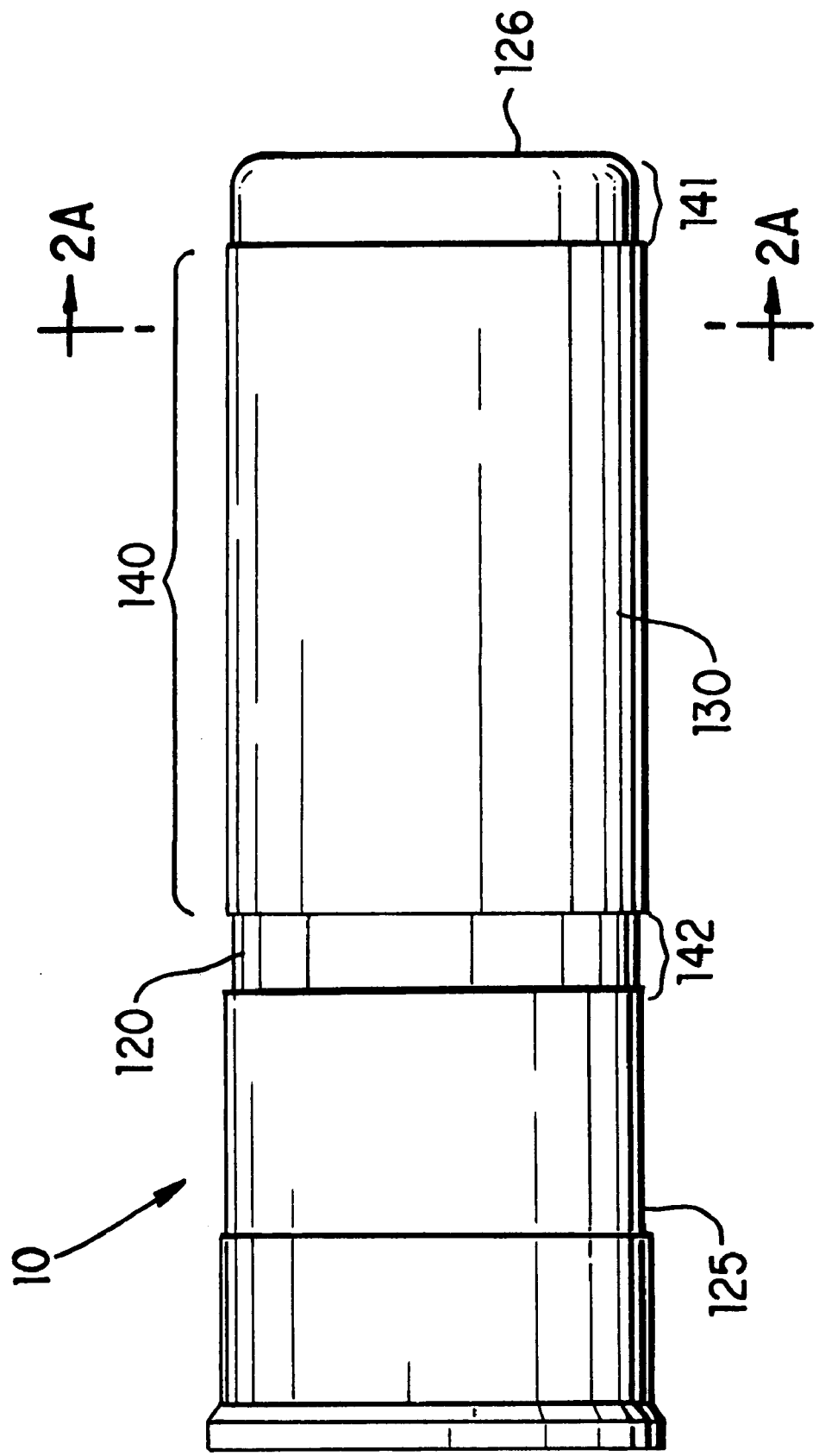
FIGS. 1A and 1B show the shotshell in accordance with the present invention.

As can be seen in FIG. 1A, a shotshell 10 includes a metallic base cap 125 having a primer (not shown). The shotshell 10 also has a hollow hull 120 that is filled with propellant, wadding, and projectiles such as pellets or a single slug (not shown). The hull 120 has a proximal end connected to the metallic base cap 125 and a terminal end away from the base cap 125, that is formed to a crimp 126 to contain the components of the shotshell. The shotshell 10 also has a layer of protective material 130. This layer of protective material 130 protects the chamber against buildup when a hull made of a material that experiences melting or softening is in the chamber. The hull 120 is not in direct contact with the chamber due to the presence of the protective material 130. Thus, the layer of protective material 130 provides a barrier between the firing chamber and the hull 120. The protective material layer 130 may be a material that has a higher melting point than the hull material 120, such as a melting point of 290° F. Such materials include paper, fiberglass and foil.

The protective material 130 may have a thickness such that the diameter is increased to reduce the clearance of the shotshell 10 in the chamber and thereby resist the shotshell sliding out of the chamber before the breech is closed. This is particularly advantageous in a firing apparatus with an elevated muzzle.

The protective layer 130 may have an adhesive surface exposed to the hull to provide a bond between the exterior surface of the hull and the protective material (see FIG. 2). This adhesive material 250 may be pressure-sensitive and prevent the protective material from becoming separated from the hull 120.

Figure 1B:
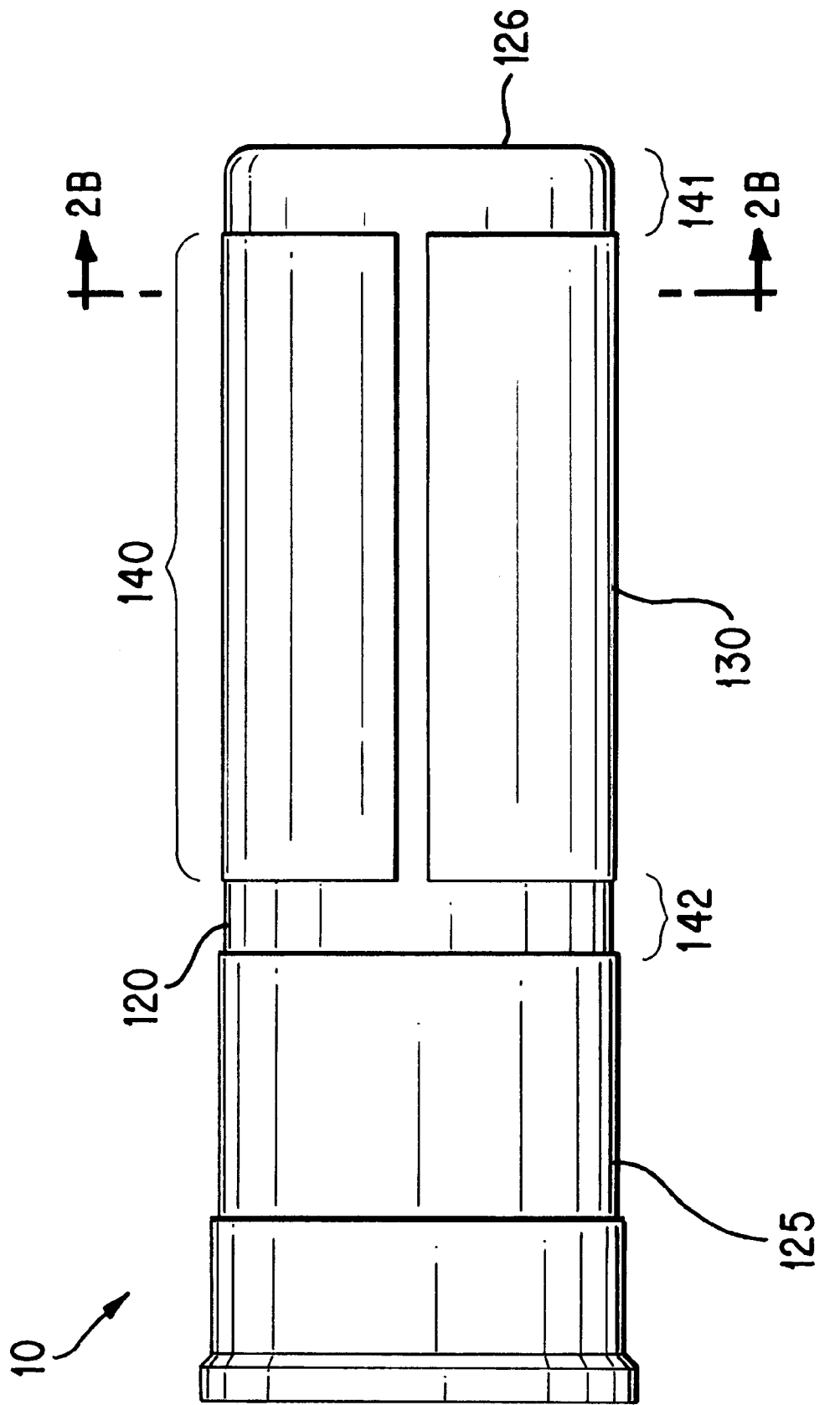

As shown in FIG. 1B, the protective layer may not completely surround the entire circumference of the hull 120.

The protective material can be deformable such that it may be wrapped around the outer surface of the hull. The wrapping process may be performed by a machine process.

The protective wrap can be precut, preprinted, and pre-applied with pressure sensitive adhesive wrap, dispensed from a roll. Applying the protective wrap from the roll can be done either in a vertical or horizontal position while the shotshell is moved along on a conveyor belt or a rotary dial type feed system, this method is presently being used in industry to apply labels to bottles, cans, and similar items.

Application of the protective layer could also be done in the production process by cutting, printing, applying adhesive, and placement of the wrap on the shotshell using either flat or rolled stock.

Another possible application could be to use a shrink wrap type procedures.

Alternatively, the protective material may be formed in a tubular-like structure that may be slid over the exterior surface of the hull. In this embodiment, the tubular-like structure may be bonded by using a material such as a free flowing adhesive or otherwise conformed to fit closely over the hull 120, so as to form an outer layer or sleeve-like configuration around the hull 120.

The layer of protective material 130 extends a distance 140 along the length of the shotshell 10. This distance 140 may be any portion including the entire axial length of the exposed portion of the hull 120 of the shotshell 10. Distance 141 represents the section from the terminal end, which may be left unprotected and typically ranges from about 1 percent to 15 percent of the length of the hull 120. Distance 142 represents the distance from the edge of the metallic base cap 125 to the protected material 130. When the exposed surface area of the hull 120 is completely surrounded by the protective material 130, there is no area of the hull 120 exposed to the chamber. At a minimum, the protective material 130 will cover approximately five percent of the exterior surface area of the hull 120.

The protective material 130 will typically be configured such that it surrounds the hull 120, in a sleeve-like manner.

The protective material 130 is also preferably non-combustible below a temperature of 400° F. to prevent the possibility of a fire in the chamber.

Figure 2A:
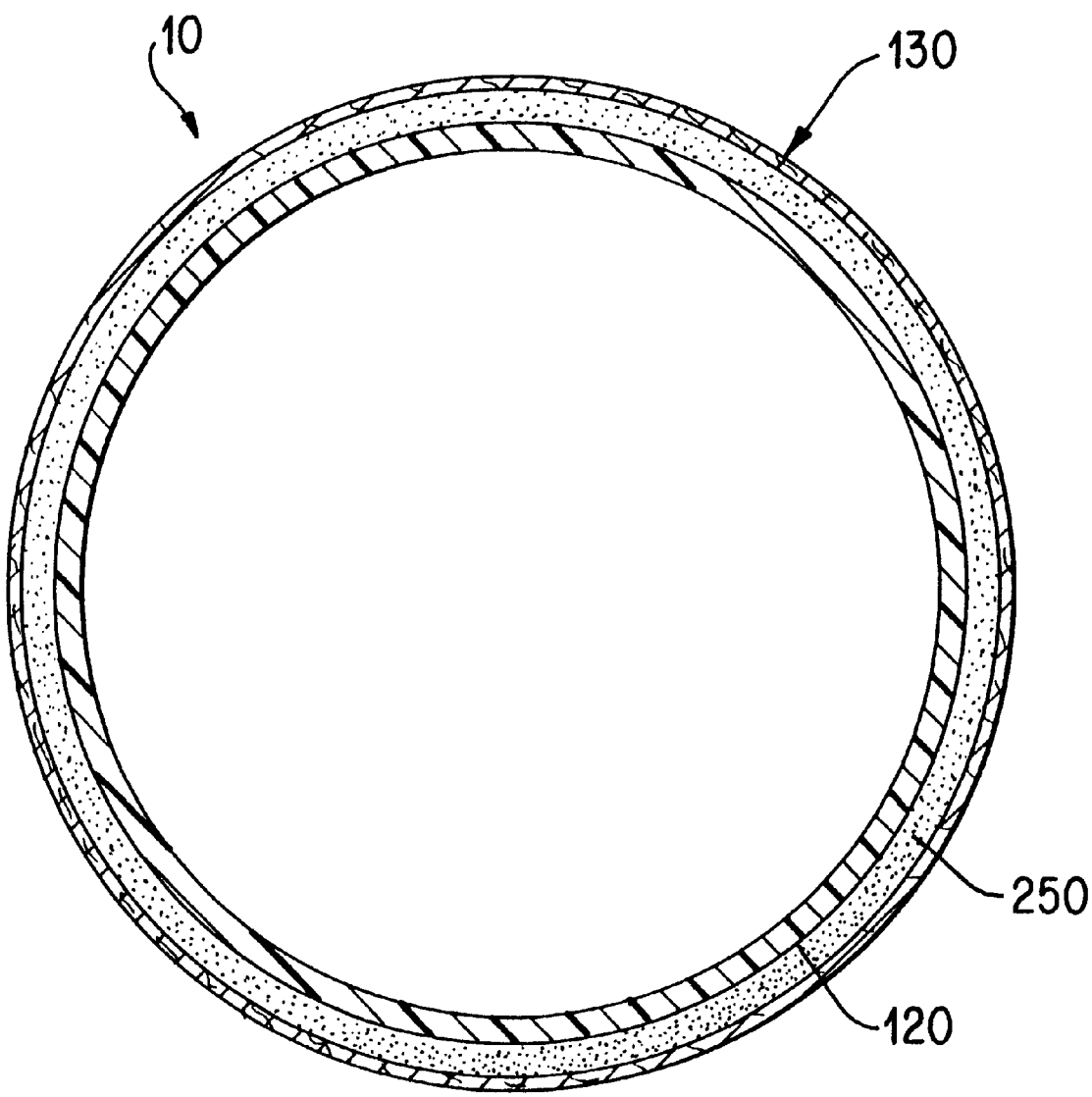
FIGS. 2A and 2B show a cross sectional view of the shotshell of the present invention.

As seen in FIG. 2A, the cross section of the shotshell 10 described herein is slightly greater with the addition of the layer of protective material 130. An adhesive material 250 may be disposed between the protective material surface exposed to the exterior hull surface and the exterior hull surface. In this embodiment, the outer diameter of the shotshell 10 will increase by the thickness of the protective material, and the adhesive.

Alternatively, the outer diameter of the shotshell 10 could be reduced, during manufacture, such that the addition of the protective layer 130 and adhesive material 250 would not cause the total outer diameter of the protected shotshell from exceeding the outer diameter of a typical shotshell that does not have a protective layer.

Figure 2B:
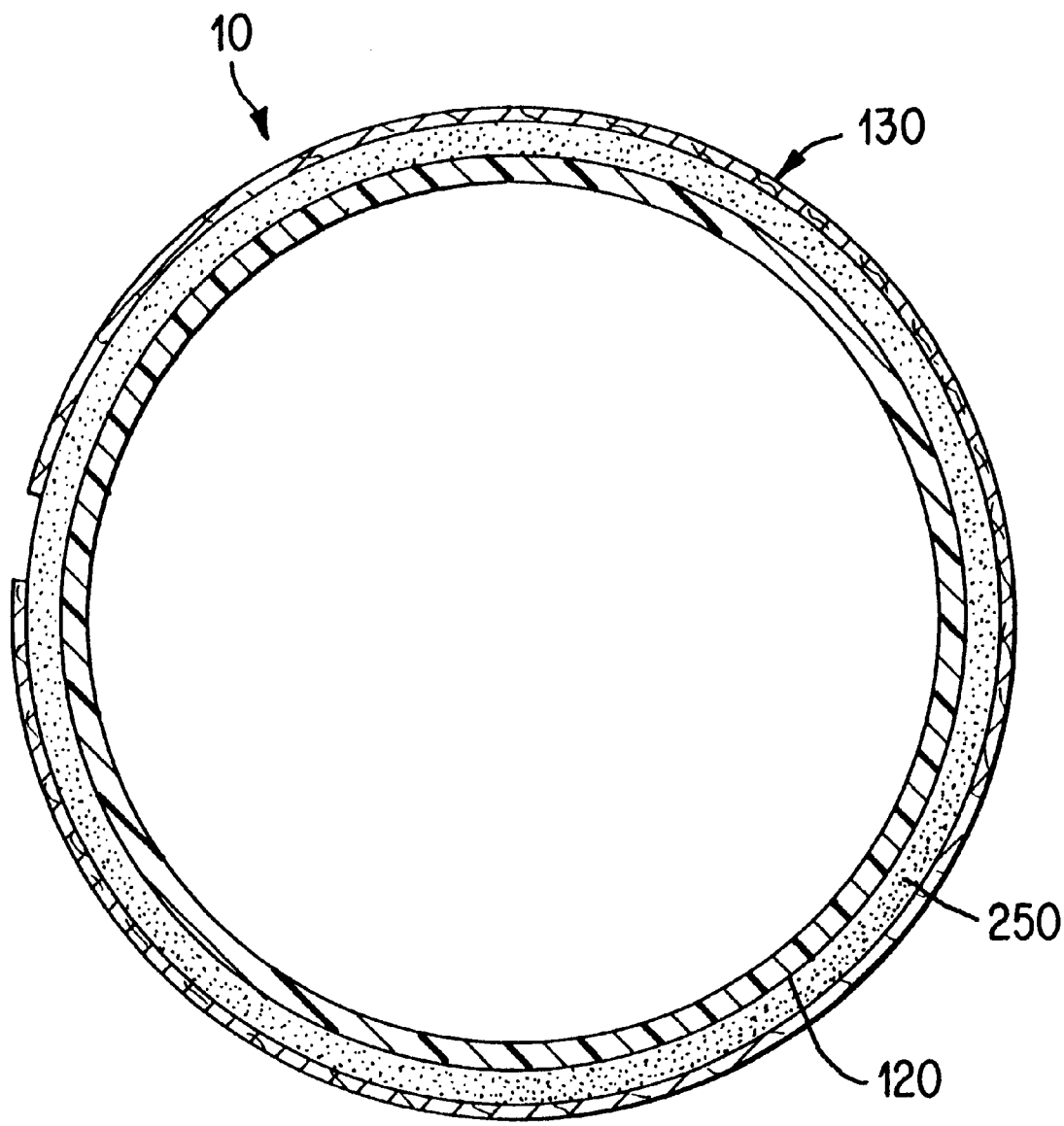

As shown in FIG. 2B, the protective layer may not completely surround the circumference of the shotshell 10. Instead, there may be a portion of the hull along the radial axis that is not covered by the protective material 130.

Figure 3:
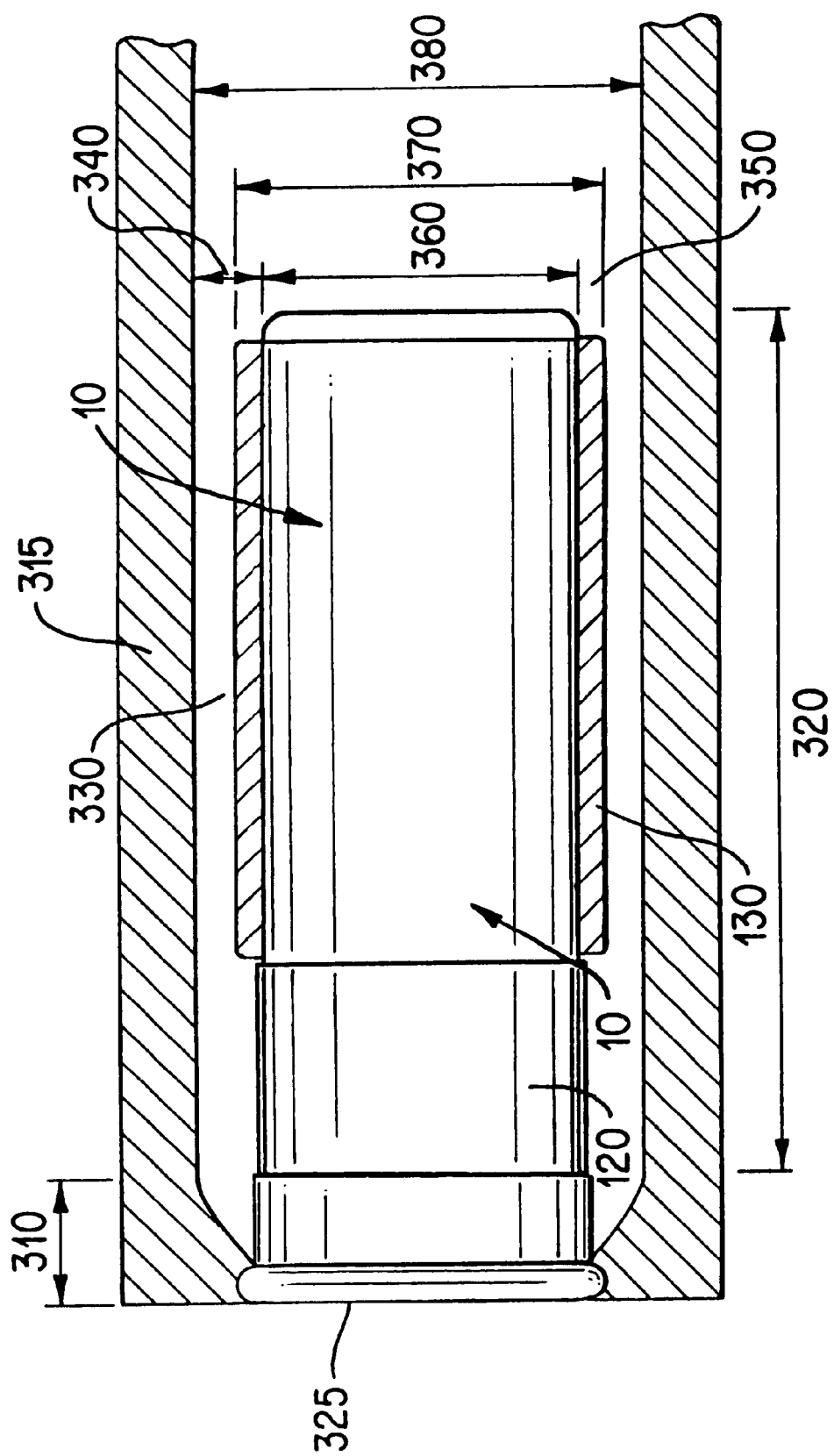
FIG. 3 shows a partial sectional view of the shotshell in a discharge apparatus taken along the X-axis.

As shown in FIG. 3, the increased diameter 370 of the shotshell 10 due to the protective material 130 does not cause the shotshell 10 to get stuck in the chamber since the chamber 315 has a clearance 330 of approximately 0.005 inches in an eight gauge barrel to accommodate variations in shotshell size. The magnitude of this clearance 330 is relative to the size of the barrel.

The shotshell 10 includes a metallic base cap 325 that may be made from brass or steel, a hull portion 120 and a protective material 130 covering a portion of the hull 120. The protective thickness is designed to minimize the increase in hull thickness.

Thus, the shotshell 10 with a protective barrier layer 130 may be used in conventional barrels without modification of the firing apparatus or apparatus malfunction.

While typical dimensions for an eight gauge shotshell in a chamber 315 are described, these dimensions are a function of barrel size and are also applicable to other larger or smaller chamber sizes used in other gauges of ammunition.

The shotshell 10 has a cap 325 attached to a hull 120 at the proximal end of the hull. The cap length 310 is approximately 0.3 to 1.3 inches depending on the design. The chamber 315 has an inner diameter greater than the combined diameter of the hull 120 and protective material 130. In this example, the outer hull diameter 360 is between about 0.89 inches and 0.91 inches. The distance between the outer surface of the shotshell and the inner surface of the chamber 330 is between about 0.005 and 0.006 inches. The inner diameter of the chamber 380 is between about 0.928 and 0.916 inches. The length of the hull 320 is about 2 inches. The thickness of the protective material 350 is between about 0.002 inches and 0.004 inches. As understood by those skilled in the art, these dimensions are a function of the size of the chamber and will vary according to the particular barrel size of a particular application and have a dimension commensurate with the clearance required for a particular application.

Figure 4A:
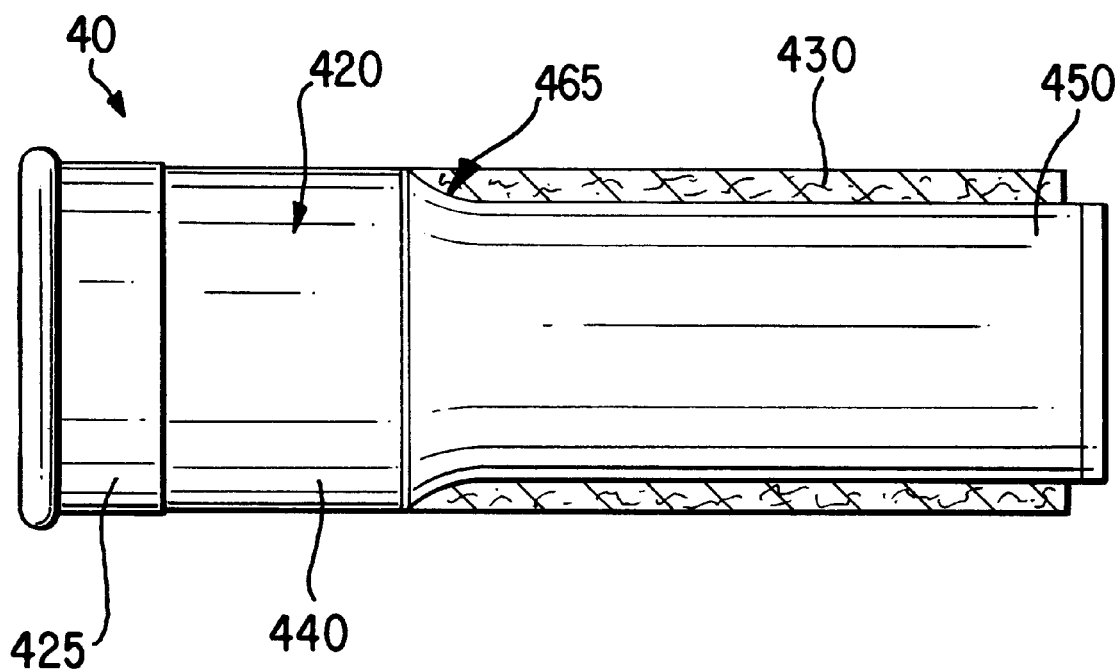
FIGS. 4A and 4B show a hull with a reduced section for receiving the protective barrier layer.
Figure 4B:
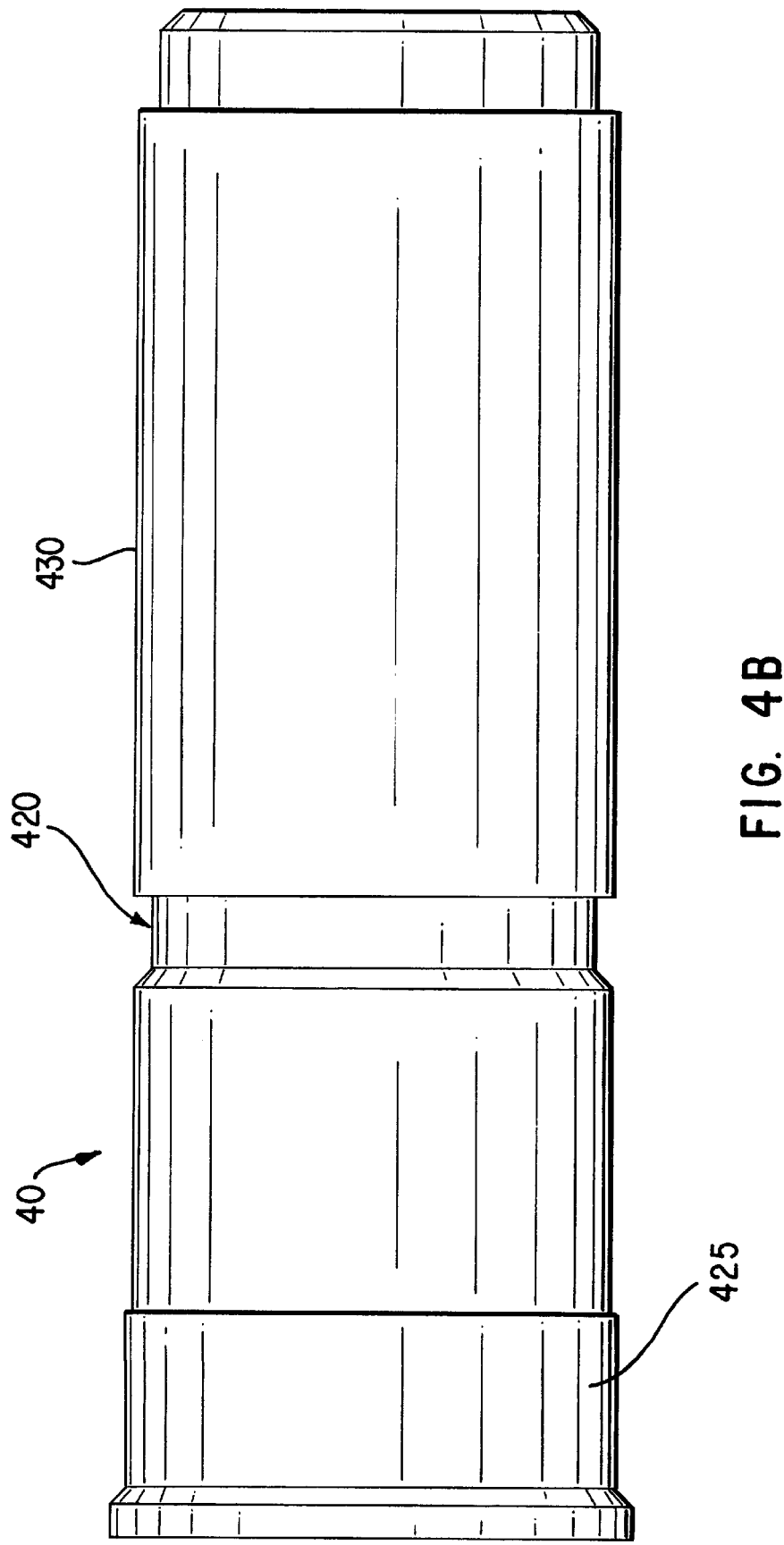

FIGS. 4A and 4B show a shotshell 40 that has a reduced diameter hull 420. This reduced diameter is between approximately 70 percent to 98 percent of the outer diameter of a conventional hull.

Thus, when the reduced diameter hull 420 is wrapped with the protective material 430, the total diameter of the hull with the protective material does not significantly exceed the outer diameter of a standard shotshell for that particular gauge. This is desirable when the clearance of a barrel is very narrow, so the increase in overall shotshell diameter will not cause a malfunction when the wrapped shotshell 40 is used with a conventional barrel.

The shotshell with a protective material layer may be used for any variety or size of hull.

While the preferred embodiments of the present invention have been illustrated in detail, it should be apparent that modifications and adaptations to those embodiments may occur to one skilled in the art, without departing from the scope of the present invention as set forth in the following claims.

What is claimed is:

1. A shotshell comprising:
   a projectile;
   a propellant charge;
   a hull having a plastic portion extending for a substantial portion of a length of the shotshell and accommodating the projectile in a front portion and the propellant charge in an aft portion;
   a metallic cap attached to the hull at an aft end of the hull; and
   a thermally protective material selected from the group consisting of paper and fiberglass and adhered to a substantially cylindrical exterior surface of the plastic portion.

2. The shotshell of claim 1 wherein said protective material adheres to at least approximately 5 percent of an exterior surface area of said hull.

3. The shotshell of claim 1 wherein the protective material is paper.

4. The shotshell of claim 1 further comprising an adhesive material disposed between the protective material and the exterior surface of the hull, for adhering the protective material to the exterior surface.

5. The shotshell of claim 4 wherein the adhesive material is pressure sensitive.

6. The shotshell of claim 1 wherein the protective material has a thickness effective to slightly increase a diameter of said shotshell.

7. The shotshell of claim 1 wherein the protective material adheres to approximately fifty percent or more of an exterior surface area of said hull.

8. The shotshell of claim 1 wherein the protective material adheres to between five percent and fifty percent of an exterior surface area of said hull.

9. The shotshell of claim 1 wherein the protective material comprises paper and has a thickness of between about 0.002 inches and about 0.004 inches.

10. The shotshell of claim 1 wherein the protective material forms a tubular structure that is slid over the exterior surface.

11. The shotshell of claim 1 wherein the protective material does not cover said exterior surface of said hull from a terminal end of said hull for a distance of between 1% and 15% of the length of the hull.

12. The shotshell of claim 1 wherein the protective material is non-combustible below a temperature of 400° F.

13. The shotshell of claim 1 wherein the protective material comprises paper, precut to a particular size such that said paper adheres to over 5 percent of a surface area of said exterior surface of said hull.

14. The shotshell of claim 1 wherein the protective material surrounds less than the entire circumference of the shotshell.

15. The shotshell of claim 1 being an industrial shotshell, dimensioned for use in an 8-gauge industrial ballistic tool and wherein said protective material is paper.

16. An industrial shell for use with an industrial ballistic tool comprising: a projectile;
   a hull having a plastic portion extending for a substantial portion of a length of the shell and having a front portion holding the projectile and an aft portion enclosing a propellant charge;
   a metallic cap attached to the hull at an aft end of the hull; and
   a thermally protective member substantially surrounding and adhered to a substantially cylindrical exterior surface of the plastic portion and comprising a material selected from the group consisting of paper and fiberglass.

17. The shell of claim 16 being dimensioned for use with an 8-gauge industrial ballistic tool and wherein said material is paper and said projectile is a single industrial slug.

18. The shell of claim 16 wherein said thermally protective member has a thickness which reduces a tendency of the shell to slide out of the chamber of the tool when a muzzle of the tool is elevated.

19. A method for preparing a shotshell for discharging from a firing chamber comprising:
   forming a hollow hull having a plastic portion having exterior and interior surfaces;
   forming a metallic cap at a proximal end of said hull for receiving a primer; and
   forming a thermally protective material layer adhering to a substantially cylindrical portion of the exterior surface wherein the protective material is selected from the group consisting of paper and fiberglass for providing the barrier between a plastic portion of the hull and the firing chamber and having substantially greater resistance to melting and softening than the plastic portion when contacted with such chamber having a temperature elevated by repeated firing and having a thickness effective to slightly increase a diameter of said shotshell.

* * * * *